(12) United States Patent  
Ezeamuzie et al.

(10) Patent No.: US 8,324,422 B2  
(45) Date of Patent: Dec. 4, 2012

(54) ENHYDRAZONE ESTERS FOR TREATING ASTHMA, ALLERGY AND INFLAMMATION

(75) Inventors: Charles I. Ezeamuzie, Athens, GA (US); Ivan O. Edafiogho, Safat (KW)

(73) Assignee: Kuwait University, Safat (KW)

( * ) Notice: Subject to any disclaimer, the term of this patent is extended or adjusted under 35 U.S.C. 154(b) by 376 days.

(21) Appl. No.: 12/662,780

(22) Filed: May 3, 2010

(65) Prior Publication Data

US 2010/0216881 A1    Aug. 26, 2010

Related U.S. Application Data

(63) Continuation-in-part of application No. 12/098,460, filed on Apr. 7, 2008, now abandoned.

(51) Int. Cl.  
*C07C 229/48* (2006.01)
(52) U.S. Cl. ..................................... 560/125
(58) Field of Classification Search .......................... None  
See application file for complete search history.

(56) References Cited

U.S. PATENT DOCUMENTS 5,468,775 A    11/1995  Scott et al.  
5,616,615 A *   4/1997  Scott et al. ..................... 514/511

OTHER PUBLICATIONS

Naringrekar et al, Journal of Pharmaceutical Science, Mechanism of Hydrolysis and Structure-Stability Relationship of Enaminones as Potential Prodrugs of Model Primary Amines, 1990, 79(2), pp. 138-146.*

Charles I. Ezeamuzie, Mary Al-Hage, "Effects of Some Anti-Asthma Drugs on Human Eosinophil Superoxide Anions Release and Degranulation", *Int Arch Allergy Immunol* 1998;115:162-168.

Greenhill et al., "Functionalized Enaminones and Their Use in Heterocyclic Synthesis", *Journal of Heterocyclic Chemistry*, 1992, 29, pp. 1375-1383.

* cited by examiner

*Primary Examiner* — Paul A Zucker  
(74) *Attorney, Agent, or Firm* — Richard C. Litman

(57) ABSTRACT

The enhydrazone esters for treating asthma, allergy, and inflammation relate to the use of two cyclohexenone derivatives and pharmaceutically acceptable salts thereof in the treatment of asthma, allergies, and inflammation. The esters have the formula:

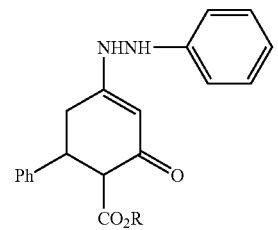

wherein R is ethyl or methyl. Administration of the esters inhibits the degranulation of eosinophils, the degranulation of mast cells, and the release or expression of tumor necrosis factor-$\alpha$, thereby alleviating the debilitating symptoms of asthma, allergic reactions, and inflammatory responses.

1 Claim, 4 Drawing Sheets

ENHYDRAZONE ESTERS FOR TREATING ASTHMA, ALLERGY AND INFLAMMATION

CROSS-REFERENCE TO RELATED APPLICATION

This application is a continuation-in-part of U.S. patent application Ser. No.12/098,460, filed on Apr.7, 2008, now abandoned.

BACKGROUND OF THE INVENTION

1. Field of the Invention

The present invention relates to the compositions for treating asthma, allergy and inflammation, and particularly to a pair of enhydrazone esters that may be used effectively in the treatment of asthma, allergy and inflammation.

2. Description of the Related Art

Drugs having anti-asthma and anti-allergic effects are well known, but such drugs are typically either bronchodilators or inhibitors, or work through the inhibition of the release of allergic mediators or inflammatory mediators. Due to the important role that eosinophils play in allergies, allergy-related diseases and asthma, drugs that have direct inhibitory effect on these cells are widely believed to hold a high potential for the effective treatment of these diseases. Previous studies, however, have shown that no existing clinically used anti-allergy or anti-asthmatic drugs, at clinically relevant concentrations, have any significant direct inhibitory effect on eosinophil degranulation.

Allergic diseases (e.g., asthma, allergic rhinitis, urticaria, atopic eczema and dermatitis) are experienced by up to 25% of the population, and the prevalence of these conditions appears to be increasing worldwide. Eosinophils and mast cells are the two most important pro-inflammatory cells involved in the pathophysiology of asthma and other allergic diseases. The degranulation of these cells and the release of many mediators, including tissue-damaging proteins, by eosinophils orchestrate the inflammation that underlies these diseases.

The primary trigger of allergic diseases is the interaction between an allergen and the specific immunoglobulin E (IgE) molecules bound to the high affinity IgE receptor (FceRI) on the surface of mast cells of sensitized patients. This results in the degranulation of these cells and the consequent release of pre-formed allergic and inflammatory mediators, such as histamine, tryptase and various enzymes. In addition, other mediators, such as eicosanoids (e.g., leukotrienes) and cytokines (especially TNF-α, IL-4, IL-13 and GM-CSF), are synthesized and released on activation. All of these mediators participate in the pathophysiology of the diseases.

Like the mast cells, eosinophils are also intimately involved in the pathophysiology of asthma. Histologically, the asthmatic lung is heavily infiltrated by eosinophils, which are believed to degranulate at the site to release mediators that contribute to bronchial inflammation, airway hyperresponsiveness, and airway tissue remodeling. Eosinophil granules contain several cationic proteins, such as major basic protein (MBP), eosinophil cationic protein (ECP), eosinophil-derived neurotoxin (EDN), and eosinophil peroxidase (EPO), which are directly toxic to many tissues. The released cationic proteins are believed to damage, in particular, the epithelium leading to bronchial hyperresponsiveness that is so characteristic of asthma. In fact, sputum eosinophil count, as well as the level of eosinophil cationic protein, has been shown to be a reliable indicator of disease severity or exacerbation. Furthermore, results from studies employing eosinophil-deficient mice strongly support an important role for eosinophils in asthma.

Drugs used as inhibitors of mast cell degranulation, such as cromolyn sodium and nedocromil sodium, are used in the treatment of asthma and other allergic diseases. Drugs that may inhibit eosinophil accumulation or inhibit cytokine generation, such as steroids, are also used as anti-asthma and anti-allergic drugs. However, no currently available drug has the ability to directly inhibit the degranulation of both mast cells and eosinophils.

Even steroids, which are the current mainstay of antiinflammatory therapy, lack an acute and direct effect on degranulation of these cells. Steroids also have many side effects.

Drugs that combine the ability to directly inhibit the degranulation of both mast cells and eosinophils at clinically relevant concentrations would be highly desirable for the treatment of asthma and other allergy-related diseases and conditions.

Thus, enhydrazone esters for treating asthma, allergy, and inflammation solving the aforementioned problems are desired.

SUMMARY OF THE INVENTION

The enhydrazone esters for treating asthma, allergy, and inflammation relate to the use of two cyclohexenone derivatives and pharmaceutically acceptable salts thereof in the treatment of asthma, allergies, and inflammation. The esters have the formula:

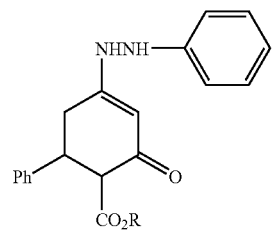

wherein R is ethyl or methyl. Both esters are stable solids at room temperature.

The ethyl ester (hereinafter referred to as CEE-1) is ethyl 4-phenylhydrazinocyclohex-3-en-2-oxo-6-phenyl-1-oate, having the empirical formula ($C_{21}H_{22}O_3N_2$) and a molecular weight of 350.3.

The methyl ester (hereinafter referred to as CEE-2) is methyl 4-phenylhydrazinocyclohex-3-en-2-oxo-6-phenyl-1-oate, having the empirical formula ($C_{20}H_{20}O_3N_2$) and a molecular weight of 336.39. The CEE-1 and CEE-2 esters may be formulated in any desired delivery form, such as a tablet, a capsule, a time-release capsule, a syrup, a liquid, an injection, a spray, or an inhalant, and may be combined with any suitable pharmaceutical carrier, vehicles, binders, fillers, disintegrators, lubricants, solubilizers, emulsifiers, surfactants, pharmaceutically equivalent salts thereof, and/or other excipients.

The inventors have found that CEE-1 and CEE-2 have the ability to act directly and potently to inhibit human eosinophil degranulation, the ability to inhibit directly and potently the degranulation (β-hexoseaminidase release) of allergen-stimulated mast cells, and the ability to strongly and directly inhibit the release of tumor necrosis factor-alpha (TNF-α) in lipopolysaccharides (LPS)-stimulated macrophages, thereby inhibiting inflammation. Thus, CEE-1 and CEE-2 are useful in the treatment of asthma and other allergic diseases, along with the treatment of other non-allergic inflammatory diseases, such as rheumatoid arthritis.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The enhydrazone esters for treating asthma, allergy and inflammation relate to the use of two cyclohexenone derivatives and pharmaceutically acceptable salts thereof in the treatment of asthma, allergies and inflammation. The esters have the formula:

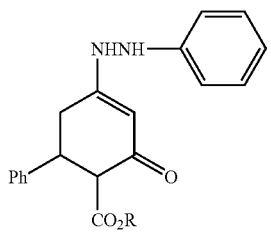

wherein R is ethyl or methyl. Both esters are stable solids at room temperature.

The ethyl ester (hereinafter referred to as CEE-1) is ethyl 4-phenylhydrazinocyclohex-3-en-2-oxo-6-phenyl-1-oate ($C_{21}H_{22}O_3N_2$), which has a molecular weight of 350.3. CEE-1 has a melting point of between approximately 150° C. and approximately 153° C., and shows characteristic ultraviolet absorption in $H_2O$ at 294 nm, in 1M HCl at 283 nm, and in 1M NaOH at 319 nm. Infrared absorption occurs at 1572 $cm^{-1}$ and 1666 $cm^{-1}$ for an O=C—C=C—N system, 1730 $cm^{-1}$ for an ester, and 3281 $cm^{-1}$ for NH. The CEE-1 ester may be formulated in any desired delivery form, such as a tablet, a capsule, a time-release capsule, a syrup, a liquid, an injection, a spray, or an inhalant, for example, and be combined with any suitable pharmaceutical carrier, vehicles, binders, fillers, disintegrators, lubricants, solubilizers, emulsifiers, surfactants, pharmaceutically equivalent salts thereof, and/or other excipients.

The methyl ester (hereinafter referred to as CEE-2) is methyl 4-phenylhydrazinocyclohex-3-en-2-oxo-6-phenyl-1-oate ($C_{20}H_{20}O_3N_2$), which has a molecular weight of 336.39. CEE-2 has a melting point of between approximately 179° C. and approximately 182° C., and shows characteristic ultraviolet absorption in $H_2O$ at 295 nm, in 1M HCl at 283 nm, and in 1M NaOH at 319 nm. Infrared absorption occurs at 1492 $cm^{-1}$ and 1569 $cm^{-1}$ for an O=C—C=C—N system, 1739 $cm^{-1}$ for an ester, and 3266 $cm^{-1}$ for NH. The CEE-1 ester may be formulated in any desired delivery form, such as a tablet, a capsule, a time-release capsule, a syrup, a liquid, an injection, a spray, or an inhalant, for example, and be combined with any suitable pharmaceutical carrier, vehicles, binders, fillers, disintegrators, lubricants, solubilizers, emulsifiers, surfactants, pharmaceutically equivalent salts thereof, and/or other excipients.

The inventors have found by in vitro testing that CEE-1 and CEE-2 have the ability to act directly and potently to inhibit human eosinophil degranulation, the ability to inhibit directly and potently the degranulation (β-hexoseaminidase release) of mast cells, and the ability to strongly and directly inhibit the release of tumor necrosis factor-alpha (TNF-α) in lipopolysaccharides (LPS)-stimulated macrophages. Thus, CEE-1 and CEE-2 are useful in the treatment of asthma and other allergic diseases, along with the treatment of other non-allergic inflammatory diseases, such as rheumatoid arthritis.

Figure 1:
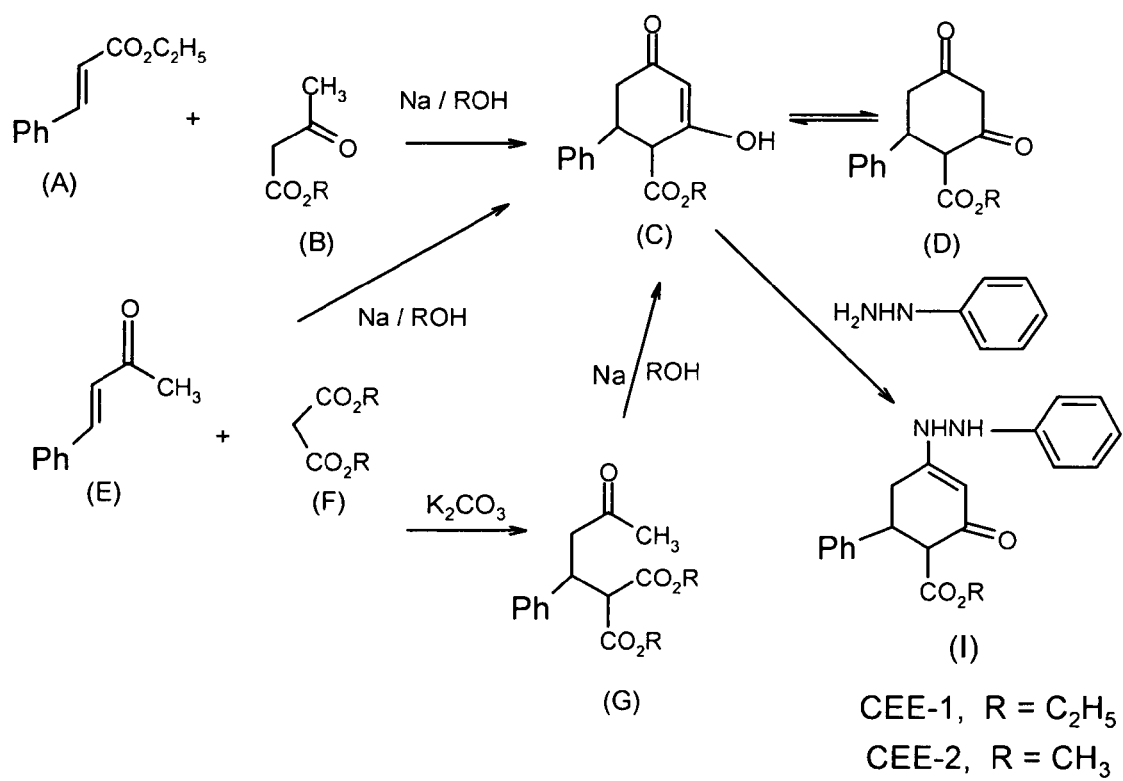
FIG. 1 shows a reaction mechanism for synthesizing CEE-1 and CEE-2.

FIG. 1 illustrates the synthesis of CEE-1 and CEE-2. The cyclization reaction between trans-4-phenyl-3-buten-2-one (A) and alkyl acetoacetate (B) in the presence of freshly prepared sodium alkoxide gives an intermediate beta-hydroxy keto ester, existing as two tautomers (C) and (D). Condensation of (C) with phenylhydrazine yields the enhydrazone esters CEE-1 (R=Et) and CEE-2 (R=Me).

Alternatively, benzylidene acetone (E) may be reacted with dialkyl malonate (F) in freshly prepared sodium alkoxide to give the intermediate beta-hydroxy keto ester (C). Another alternative route involves the reaction of (E) and (F) under mild conditions with potassium carbonate to give the adduct (G), which is then cyclized in freshly prepared sodium alkoxide to give the intermediate beta-hydroxy keto ester (C). Any of these three routes provides for the synthesis of the intermediate beta-hydroxy keto ester (C), and condensation with phenylhydrazine yields CEE-1 (R=Et) and CEE-2 (R=Me).

EXAMPLE 1

Example 1 involves the testing of the effect of complement C5a-induced degranulation of human blood eosinophils, and IgE-dependent degranulation of mast cells. Human peripheral blood eosinophils were purified to >98% by the immunomagnetic method. Aliquots containing $2.5 \times 10^4$ cells were added to each well of a 96-well microplate. The cells were separately pre-incubated for 10 minutes with CEE-1, CEE-2 or the drug solvent (DMSO) and then subsequently stimulated with recombinant human complement C5a (30 nM) in the presence of cytochalasin B (5 μg/mL). The reaction was allowed to proceed for 30 minutes at 37° C. The amount of the granular eosinophil peroxidases (EPO) released into the supernatant (as index of degranulation) was determined by the o-phenylenediamine method. The amount of EPO released was expressed as a percentage of the total cell content.

Figure 2:
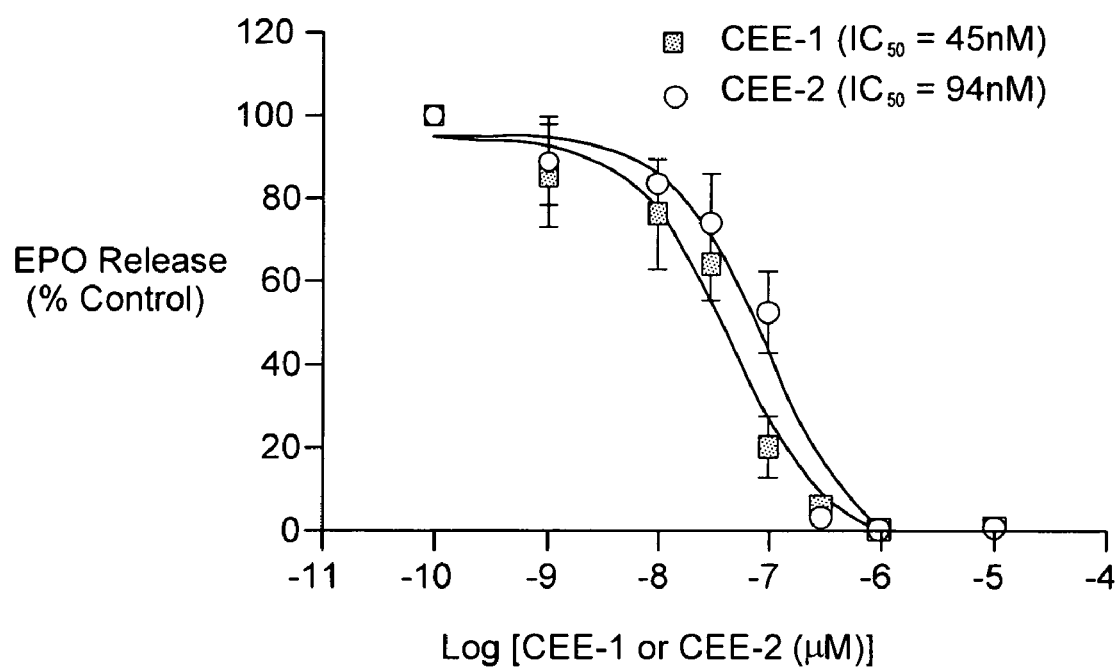
FIG. 2 is a chart showing inhibition of complement C5a-stimulated degranulation (EPO release) of human eosinophils as a function of the concentration of CEE-1 and CEE-2.

FIG. 2 displays the inhibition of complement C5a-stimulated degranulation (EPO release) of human eosinophils by CEE-1 and CEE-2. Cells were incubated with the each of CEE-1 and CEE-2 for 10 minutes before stimulation. Control uninhibited releases were in the range of 20-30% of total cell content. Results are shown as mean±SD, n=4.

In untreated cells, C5a induced the release of 20-30% of the total cellular content of EPO. As shown in FIG. 2, pre-treatment of the cells with CEE-1 or CEE-2 resulted in a potent and highly effective inhibition of the EPO release. The concentration achieving 50% inhibition was 45 nM and 94 nM for CEE-1 and CEE-2, respectively, and at the concentrations of 300 nM and above, both CEE-1 and CEE-2 completely abolished EPO release. Even at concentrations that abolished release, both compounds did not significantly affect the viability of the cells, thus ruling out cellular toxicity as the cause of the inhibition.

EXAMPLE 2

Example 2 involves the testing of the IgE-dependent degranulation of mast cells.

The anti-allergic effect was tested on IgE-dependent mast cell degranulation using the rat basophilic leukemia (RBL-2H3) cell line model. The cells were passively sensitized with 0.5 μg/mL anti-DNP monoclonal IgE antibody for 1 hour, and then washed twice to remove unbound antibody. They were then separately pre-treated with CEE-1, CEE-2 or their solvent (DMSO) for 10 minutes before being stimulated with the specific antigen DNP-BSA (100 ng/mL). After 30 minutes of incubation, the amount of granular β-hexoseaminidase released into the supernatant (index of degranulation) was determined photometrically.

Figure 3:
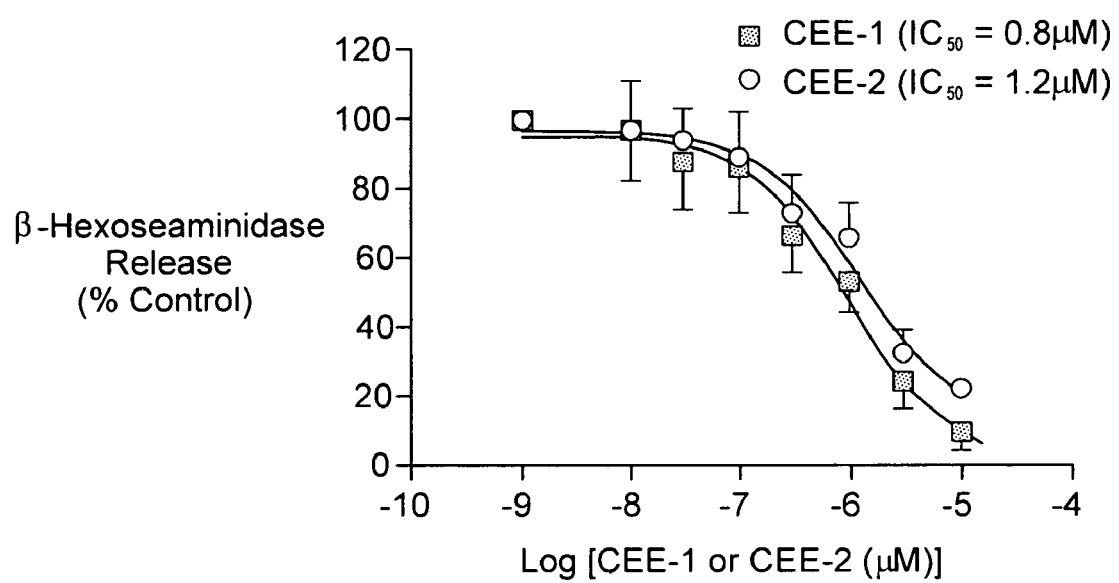
FIG. 3 is a chart showing inhibition of antigen induced IgE-mediated degranulation (β-hexoseaminidase release) of mast cells (RBL-2H3) as a function of the concentration of CEE-1 and CEE-2.

FIG. 3 illustrates the inhibition of antigen induced IgE-mediated degranulation (β-hexoseaminidase release) of mast cells (RBL-2H3) by CEE-1 and CEE-2. Cells were incubated with CEE-1 and CEE-2 for 10 minutes before stimulation. Control uninhibited releases were in the range of 15-26% of total cell content. Results are shown as mean±SD, n=3.

As shown in FIG. 3, pre-treatment of passively-sensitized RBL-2H3 mast cells with CEE-1 and CEE-2 resulted in a strong concentration-dependent inhibition of β-hexoseaminidase release (index of degranulation). The concentrations achieving 50% inhibition were 0.8 μM and 1.2 μM for CEE-1 and CEE-2, respectively. At the highest concentrations, both CEE-1 and CEE-2 showed no cellular toxicity as determined by a trypan blue exclusion test.

EXAMPLE 3

The antiinflammatory effect of CEE-1 and CEE-2 was tested on LPS-stimulated release of tumor necrotic factor-α (TNF-α) from mouse peritoneal macrophages. Thioglycollate-induced peritoneal macrophages were obtained by peritoneal lavage of Balb c mice. Macrophages purified by adherence to plastic plate were cultured in a supplemented RPMI medium and pre-treated with CEE-1, CEE-2 or their solvent (DMSO) for 30 minutes before being stimulated with LPS (1 μg/mL) for 18 hours. The amount of TNF-α released into the supernatant was determined by ELISA using commercially available kits.

Figure 4:
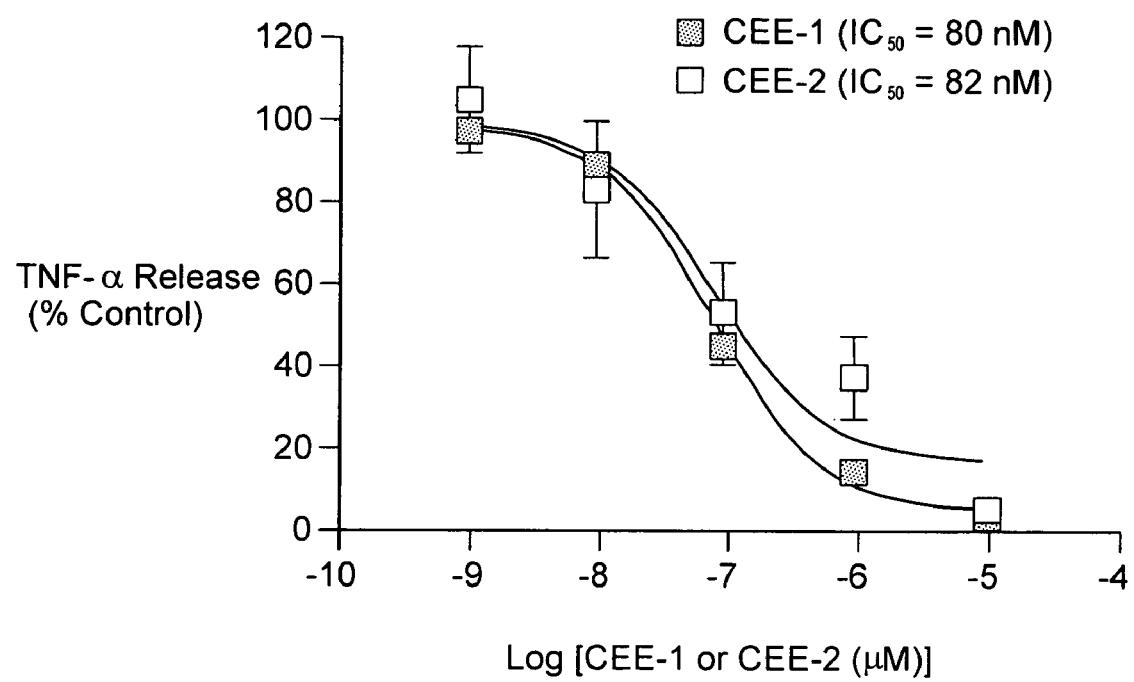
FIG. 4 is a chart showing the inhibitory effect of CEE-1 and CEE-2 on the release of TNF-α from LPS-stimulated mouse peritoneal macrophages.

FIG. 4 illustrates the inhibitory effect of CEE-1 and CEE-2 on the release of TNF-α from LPS-stimulated mouse peritoneal macrophages. Cells were pre-treated with the drugs for 30 minutes before stimulation with LPS (1 μg/mL). The net uninhibited releases were in the range of 130-185 pg/ml. Values are shown as mean±SD, n=3.

As shown in FIG. 4, treatment of the cells with CEE-1 and CEE-2 strongly inhibited the release of TNF-α in a dose-dependent manner. The concentrations of the compounds that achieved 50% inhibition of the response were 80 nM and 82 nM for CEE-1 and CEE-2, respectively. At 10 μM, both compounds completely abolished the release. Overnight incubation of these cells with both CEE-1 and CEE-2 showed no effect on their viability.

It is well known to those of ordinary skill in the art that an inflammatory response is frequently mediated by the expression of cytokines, including tumor necrosis factor-α. While the inflammatory response is ordinarily beneficial to the host, nevertheless, the inflammatory response can produce debilitating symptoms or may be excessive, regardless of the etiology of the inflammatory response, which may occur in both allergic reactions and in non-allergic, conditions, such as rheumatoid arthritis. Consequently, an antiinflammatory agent, including one that inhibits the release or expression of TNF-α, may form a part of the treatment regimen. The results in Example 3 show that the CEE-1 and CEE-2 esters may be effective antiinflammatory agents for any condition producing an inflammatory response.

It is anticipated that the ester salts of the enhydrazone esters would exhibit the same pharmaceutical properties and effects as the pure esters.

It is to be understood that the present invention is not limited to the embodiment described above, but encompasses any and all embodiments within the scope of the following claims.

We claim:
1. A compound having the formula:

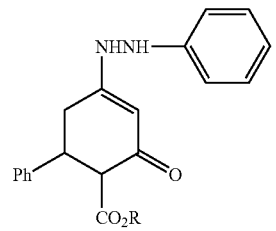

wherein R is ethyl or methyl, and pharmaceutically acceptable salts thereof.

* * * * *